United States Patent [19]

Bichon

[11] 4,161,948
[45] Jul. 24, 1979

[54] SYNTHETIC MEMBRANE FOR WOUND-DRESSINGS

[75] Inventor: Daniel Bichon, Gaillard, France

[73] Assignee: Battelle Memorial Institute, Carouge, Switzerland

[21] Appl. No.: 869,688

[22] Filed: Jan. 16, 1978

[30] Foreign Application Priority Data

Jan. 18, 1977 [CH] Switzerland ............... 576/77

[51] Int. Cl.$^2$ ............................................. A61F 13/00
[52] U.S. Cl. .................... 128/156; 428/305; 427/2; 156/326; 428/474
[58] Field of Search ............. 428/474.7, 476.3; 427/2; 156/326; 128/156, 260; 260/296 B

[56] References Cited

U.S. PATENT DOCUMENTS

| 3,849,238 | 11/1974 | Gould et al. | 128/156 X |
| 3,867,520 | 2/1975 | Mori et al. | 128/156 X |
| 3,875,937 | 4/1975 | Schmitt et al. | 128/156 |
| 3,978,266 | 8/1976 | Lock | 128/156 UX |
| 3,978,855 | 9/1976 | McRae et al. | 128/156 |
| 4,060,081 | 11/1977 | Yannas et al. | 128/156 |

FOREIGN PATENT DOCUMENTS

2150695  4/1973  France ..................... 128/156

*Primary Examiner*—Robert E. Bagwill
*Attorney, Agent, or Firm*—Finnegan, Henderson, Farabow & Garrett

[57] ABSTRACT

Artificial membrane for wound-dressings composed of two polypeptide layers, one of which at least, the inside layer which contacts the wound, is biologically resorbable and the outside layer has an asymmetric structure permeable to water and to drug solutions but pratically impervious to outside pathogenic agents. The inside layer, at least, is constituted from biodegradable copolymers of amino-acids and -diacids of which the —COOH functions are partially esterified with mono and/or di-ols.

20 Claims, No Drawings

SYNTHETIC MEMBRANE FOR WOUND-DRESSINGS

The present invention concerns a synthetic tissue or membrane containing poly-aminoacids which, because of its nature, is called an "artificial skin." The invention also concern the use of such "skin" as wound-dressings the material of which is resorbed, in situ, by human or animal bodies and a process for the manufacturing of this product.

Indeed, the membrane or "artificial skin" of the invention can be advantageously used as wound-dressing since it is resorbed, at least partly, by biodegradation, when staying in contact with living animal or human bodies and because it forms non toxic degradation products which are assimiliable by the said living bodies. This product may also advantageously have the property of improving the healing capacity of the living tissues.

The artificial skin of the invention has the further advantage, when compared to usual wound-dressings, not to have to be periodically replaced by a fresh dressing and it can be left in place on the wound to be cured and protected because of this biodegradability property. This artificial skin is therefore progressively resorbed by the organism, in full or at least to the extent concerning the portion directly applied on the wound, this resorption occurring during the healing of the wound. This phenomenon, therefore, remedies one of the main difficulties inherent to non-degradable dressings, that is, the periodical renewal of said dressings by pulling away the strips which is uncomfortable for the patient and slows down the healing process.

Another object of the invention is to provide an artificial skin with several of the favorable properties of natural skin, that is, to combine a good retention for aqueous liquids with a high porosity; this property will ensure that the living tissues are well oxygenated by the air through the membrane, that the drugs in the form of ointments or aqueous solution will readily penetrate therethrough, although the penetration of undesirable microorganisms such as fungi, germs, yeasts and viruses will be effectively prevented.

The advantages of wound-dressings which can be resorbed, at least partly, by living bodies are already known.

Thus, French Patent No. 1,593,518 (PARACHEM CORP.) discloses a wound-dressing comprising two layers of a material which is resorbable by the human body. Of these two layers, the one in contact with the wound is porous. The material of which this dressing is formed is based on cellulose derivatives. Both layers of this wound-dressing can either have a dense structure or a lighter "porous and aerated" structure. This lighter form has a better hemostatic activity than the denser form, however the denser form has a better retention power for liquids than the lighter form. Thus, this dressing simply offers a more or less efficient retention capacity for the fluids leaking from a wound and a mechanical protection against germs in complete analogy with older conventional dressings. It however offers the advantage of being resorbable, at least partly, by the organism.

U.S. Pat. No. 2,682,872 (BOWER) discloses a wound-dressing consisting of a "dried organic material" which is absorbable by the fluids of living tissues. This comprises two layers of which the first one is directly applied to the wound and has a porous structure. The second layer which is outside of the first one is "relatively non-porous" and comprises the same organic matter as the first one but the material of this second layer is placed in a "less absorbable" condition than for the first layer. This "dried organic material" preferably comprises animal blood constituents. Consequently, this wound-dressing also offers the advantage, as in French Pat. No. 1,593,518, that it is at least partly resorbable by human bodies but it either does not possess the selective permeability property which, as mentioned heretofore, is one of the main objects of the present invention.

Another reference, French Patent Application No. 2,150,695 (AJINOMOTO) concerns a process for manufacturing an artificial skin consisting of poly-aminoacids or related substances. This reference discloses the use, as polymeric amino-acids, of film forming copolymers of amino-diacids and esters thereof further crosslinked by means of di-isocyanates; as such, a copolymer of methyl $\beta$-L-aspartate and L-leucine, the ester groups of which having been saponified or, further, a copolymer of methyl $\gamma$-L-glutamate and D,L-methionine, both of these copolymers being easily resorbed by living tissues, are being mentioned. However, these products have some drawbacks; for instance, isocyanates are not desirable in the case of bio-compatible products for reasons of possible toxicity. Further, although the films obtained from the copolymers disclosed in the above reference have a high permeability for oxygen and aqueous solutions of dissolved substances such as aminoacids, salts, glucose and urea, they do not combine, as does the skin of the invention, a good retention property for the body fluids with a high permeability for gases and they do not simultaneously ensure the ready passage of drugs therethrough while preventing the penetration of pathogenic microorganisms such as germs and viruses.

In contrast, the present invention provides an artificial skin at least partly resorbable by living tissues and having, as mentioned hereinbefore, some properties very similar to that of natural skin.

Thus, the artificial skin of the invention that consists of two integral layers of which at least one is resorbable by the body, the first internal layer being directly applied to the wound and the second layer constituting an external protection thereof, is characterized by the fact that the second layer is formed from a porous semipermeable membrane or film having an asymmetric structure, that is having pores of decreasing size going from the inside to the outside, which ensures a free penetration for air, water and low molecular weight substances but prevents the entrance of external pathogenic germs and by the fact that the first layer is essentially formed from a hydrophilic, non-toxic, bio-degradable membrane consisting substantially of a cellular, spongy and fluid-permeable material selected from polymers and co-polymers of $\alpha$-aminoacids and esters thereof.

Thus, the artificial skin of the invention distinguishes from the prior-art of wound-dressings comprising components resorbable by living tissues by its novel structure which comprises two distinct layers that, although they may be made of rather similar substances, have each a specific texture and a specific function and that cooperate together so as to provide a unique combination of properties which is not found in the products of the prior-art.

As film-forming polymers and co-polymers of α-aminoacids and esters, one can use all the appropriate known substances of this type, preferably including acids and esters from α-aminodiacids. Such polymers and co-polymers are known synthetic film-forming macro-molecular products the preparation of which is disclosed in the scientific literature, e.g. "Synthetic Polypeptides," Bamford, Elliott and Hanby, Academic Press, New York (1956); "Advances in Protein Chemistry" 13, 243 and following pages (1958). As for the esters of aminodiacids, one can use the easily hydrolyzable lower alkyl esters, e.g. methyl and ethyl esters.

It is possible to use the same resorbable type polymer for forming the two layers of the present artificial skin although, naturally, the manufacturing processes are different for each layer. However, it is preferred in general, to use two different, although chemically related, polymers in order to achieve optimal mechanical and physico-chemical properties for each layer, since optimal properties for the internal layer are different from optimal properties for the external layer. Thus, the first or internal layer which will be the layer in contact with the wound is preferably made from a copolymer of L-leucine and a L-glutamate or L-aspartate ester, this ester being at least partially saponified. This co-polymer may contain from 10 to 50 mole % of leucine, the rest being a partially esterified α-L-glutamic and/or aspartic acid compound. The ratio of the leucine component to the diacid component will be determined by the rate of biodegradation desired for the copolymer. Indeed, it is known that poly-L-leucine degrades slowly whereas poly-glutamic or -aspartic acid degrades more rapidly. Therefore, copolymers of the present type with a high ratio of leucine will degrade less rapidly than copolymers with a smaller content of leucine and vice-versa. It is further preferable that the copolymer of the first layer is cross-linked to a certain extent to improve the strength of the spongy film. Innocuous cross-links are better provided by an amount of cross-esterification with a diol, namely with polyoxyethylene glycol. Such copolymer offers the advantage to have properties resembling those of natural human collagen. Preferably, the thickness of this first layer is about 0.5–3 mm, but this is only indicative.

For preparing this first layer or film, the following technique can be used: One starts by preparing a co-polymer from N-carboxy-anhydrides of amino-acids or -esters. For instance, one will select L-leucine and a β-alkyl ester of L-aspartic acid; the N-carboxyanhydrides are themselves obtained by the action of phosgene on the free amino-carboxylic acid functions of such materials. Preferably, the polymerization rate is increased with sodium hydride. In the case of the aspartic type co-polymer, one uses, as the starting material, β-benzyl aspartate since it is easily available and its N-carboxy-anhydride is easy to polymerize (actually the corresponding methyl ester does not polymerize well although the N-carboxyanhydride of γ-methyl glutamate does polymerize easily).

Thereafter, the benzylated copolymer thus obtained is trans-esterified into its corresponding methyl ester because the benzyl-copolymer would be too difficult to saponify when subjected to subsequent mild alkaline hydrolysis. The trans-esterification is carried out by usual techniques, e.g. by dissolving in MeOH in the presence of $H_2SO_4$ according to Polymer (1975) 16, 735. Of course, if in place of the benzyl asparate derivative one has used the methyl glutamate derivative which polymerizes and hydrolyzes well, no trans-esterification is needed.

Thereafter, one forms a paste by mixing the co-polymer with an organic solvent and a salt which is hydrosoluble but insoluble in this organic solvent. Such salt can be for instance NaCl or any other non toxic salt; the paste is spread on a plate and dried in layer form until the solvent has evaporated. Then, the layer is subjected to hydrolysis in dilute NaOH mixed, as a water solution, with a hydrophilic solvent. Under such conditions, a significant portion of the ester groups are converted to sodium carboxylate groups. Then, the plate is subjected to cross-linking, e.g. by dipping into an acidified ($H_2SO_4$) glycol solution, for instance into polyoxyethylene glycol of average molecular weight around 300. This cross-linking operation imparts to the layer a good mechanical resistance and flexibility. Finally, the plate is thoroughly washed with water for eliminating all water-soluble products including the salt particles the dissolution of which will provide the voids in the polymer which characterize the desired cellular spongy structure of the film. Finally, the plate is dried to give a flexible and strong film of the desired thickness. The spongy and flexible texture of this first layer ensures that it is able, when applied to a living tissue, to follow the movements thereof and to properly adhere thereto during the fibroblastic growth involved in the course of the healing process.

In order to form the second layer (that layer which protects the first one from external agents), one preferably uses a copolymer of L-leucine and γ-alkyl glutamate and, more preferably, a copolymer containing a 1:1 mole ratio of these two compounds. Preferably, this second layer will be around 50–100μ thick.

The assymmetric semi-permeable structure of this second layer which may resemble ultra-filtration or inverse-osmosis membranes is known per se (see for instance "Polymer Sciene and Technology", Vol. 6, 459 (1974), Plenum Press; "Synthetic Polymeric Membranes" by R. E. Kesting, McGraw and Hill (1971). This structure is provided with pores with variable diameters, these pores tapering down in a direction perpendicular to the surface of the layer. In the artificial skin of the invention, the second layer is arranged over the first one in a position for having the pores in the second layer to taper down in the direction going from the inside of the skin toward the outside thereof.

This second layer can be prepared very simply as follows: one spreads on a glass plate a layer of a viscous solution of the above mentioned 1:1 polymer in a water-soluble solvent, e.g. dimethylformamide (DMF); this layer is allowed to equilibrate a few minutes in air and then it is immersed in cold water until the solvent is eliminated from the layer by diffusion. The layer is then dried in warm air. One obtains then a flexible plastic layer the porosity of which can be viewed with the microscope when observing that surface in contact with the glass plate but with very thin pores openings on the opposite surface. Such openings are actually so small that they are practically undepictable even under the larger magnification factors.

Regarding now the rejection power of this layer (this term characterizes, in the ultrafiltration or inverse osmosis techniques, the percent of retention of a given substance in solution), which of course essentially depends on the size of the pores on the external side, it amounts to practically zero for low molecular weight substances, e.g. $H_2O$ or NaCl, to an average value of about 30–50% for molecules of average weight about 1000–5000 and to about 100% for macromolecular substances, e.g. water-soluble resins (Mw ≧ 20,000).

Hence, low or medium molecular weight substances such as aqueous solution of drugs or ointments can travel across the outside layer of the present artificial skin, which property is very useful when the present artificial skin is applied as a wound-dressing, whereas larger entities like bacteria, virus and other germs are effectively kept apart from the wound. The permeability of the second layer to water or aqueous solution may correspond, for instance, to about 50 ml H$_2$O per m$^2$ and per hr. under a pressure of 120 mm Hg in the direction going from the first layer of the skin toward the outside.

The process for manufacturing the artificial skin of the invention comprises applying over the first layer, after said first layer has been formed, the second layer or the substance of said second layer in a manner such that the surface of the later having the coarser porosity will adhere to the first layer.

According to one embodiment of said process, one deposits on one of the surfaces of the first layer a glueing solution containing a N-carboxyanhydride of an aminoacid dissolved in an organic solvent, one removes the second layer from its supporting plate on which it has been previously prepared, one stacks the second layer, lower side down, over the surface of the first layer coated with the adhesive with application of slight pressure and one allows the completed composite to dry until all solvent of the adhesive has evaporated. Therefore, the binding portion between the two layers will involve that surface of the second layer with the coarser pores. Thereafter, the terminated artificial skin is sterilized by usual means (heat, irradiation, etc.).

As the N-carboxyanhydride adhesive and the organic solvent, one can use glycine-N-carboxyanhydride and ethyl acetate.

According to another embodiment of the present process, one operates as follows: when the first layer has been prepared as described hereinbefore, one spreads thereover a solution of the copolymer of the second layer dissolved in a water-soluble solvent. Then, after equilibrating, the composite is immersed into ice-water for a sufficient time to cause the solvent to diffuse completely outside the polymer and the second layer to solidify. As water-soluble solvent, tetrahydrofurane (THF), dioxane, pyridine, etc. can be used.

It must be remarked that the unique structure of the present artificial membrane may be responsible for its apparent anisotropic permeability. In other words its permeability for water and other light fluids seems to be larger in the inside toward outside direction than in the opposite direction. As a consequence, the leaking of water or other fluids from the healing wound is facilitated without disturbing said wound and with no detriment to other properties of the artificial skin.

The artificial skin or membrane of the invention can be used advantageously to treat all kinds of wounds, namely in the case of injuries with loss of tissues, shocks, burns, bed sores, etc. or in case of skin grafts. When the present skin is used as a resorbable wound-dressing, the two layers thereof can be resorbed successively completely by the contacting living tissues. As a modification, it is also possible that the first thick spongy layer is absorbed and the second protective layer must be thereafter removed. In such case, this second layer (the one with asymmetrically permeable structure) is only used as a temporary protective layer.

In the first modification, no removal of part of the wound-dressing is required and, in the second modification, the final pealing of the superficial thin outside layer can be done at the time when the healing has been completed or nearly so. Therefore, the operation is painless and does not retard the healing process.

The following Examples will illustrate the invention in more details.

EXAMPLE 1

(A) Preparation of the first internal layer (methyl glutamate-leucine type)

(a) Preparation of γ-methyl-L-glutamate-N-carboxyanhydride

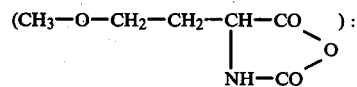

In a laboratory vessel equiped with a stirrer, a thermometer and a reflux condenser cooled with a 0°–2° C. refrigerating mixture, there were placed 250 g of γ-methyl-L-glutamate and 3 l. of tetrahydrofurane (THF). Under stirring at 40° C., phosgene was introduced at a rate of about 1 l/min. After 1 hr., the flow of COCl$_2$ was reduced to about 0.5 l/min. and this was continued for an hr. Thereafter, the solvent and excess COCl$_2$ were distilled off under reduced pressure and 278 g (93%) of the desired N-carboxyanhydride crystallized out (M.p. 99° C.). This synthesis was adapted from: "Biopolymers" 15 (1976), p. 1869.

(b) Preparation of the L-leucine-N-carboxyanhydride: The same procedure described above was followed using 200 g of leucine and there was obtained 215 g (90%) of the desired anhydride.

(c) Polymerization of a mixture of the N-carboxyanhydrides of γ-methyl-L-glutamate and L-leucine: 59.8 g of γ-methyl-L-glutamate-N-carboxyanhydride and 27 g of the L-leucine corresponding N-carboxyanhydride were dissolved in 2000 ml of dry benzene. Mole quantities of the reagents were calculated for having 65 mole % of the glutamic monomer and 35 mole % of the other monomer. Then, 240 mg of triethylamine (initiator) and 6 g of NaH (catalyst) were added under stirring at 20° C. The polymerization was allowed to go to completion during a period of 24 hrs. Then, the reaction mixture was poured under violet agitation into 5 liters of cold ethanol whereby NaH was destroyed and the polymer precipitated. The latter was collected, dried and redissolved in dichloroacetic acid (DCA), then the solution was again treated with an excess alkohol which precipitated the polymer in pure form. In this form, the polymer was soluble in organic solvents such as CHCl$_3$, THF, CH$_2$Cl$_2$ (Helix forming solvents). Yield 60 g (90%).

(d) Preparation of the cellular material: 0.5 g of the polymer prepared as described above was dissolved in 1.5 ml of CHCl$_3$ and 2 ml of benzene and 4 g of finely ground NaCl were added thereto. The resulting paste was homogenized with a ball-mill and a layer thereof (2 mm thick) was spread on a polytetrafluoroethylene (PTFE) plate. Then, the layer was dried at 60° C. in air until the solvents had evaporated.

(e) Alkaline hydrolysis and cross-linking: The PTFE plate coated with the polymeric layer was dipped at room temperature into a stirred solution of 10 ml NaOH 1N, 70 ml EtOH and 20 ml acetone. The plate was maintained therein for 17 hrs. Then, the plate was drained, it was dried 5 hrs. at 50° C. and it was again immersed into 100 ml of polyoxyethylene glycol 300 containing 5 g of $H_2SO_4$ 98% (0.5N solution). After 24 hrs. at 70° C., the plate was thoroughly washed with water until all traces of acid and salts had disappeared, then it was dried in the oven at 70° C. The spongy material thus prepared is flexible and tough, it is insoluble in DCA but soluble in NaOH 0,1 N. It was analyzed by dissolving a sample in an aliquot of alkali and back titrating with HCl (Phenolphthalein); as a result, it was found that 59% of the original methyl groups were saponified and converted to —COOH groups.

If, instead of subjecting the above hydrolyzed polymer to cross-linking, with the PEG-$H_2SO_4$ solution, it was simply neutralized with a 3% $H_2SO_4$ solution in PEG, there was obtained a material which, after drying, was soluble in DCA and mechanically brittle.

It will be noted that, by using the above procedure outlined under (a) to (d), other polymers based on methyl glutamate and leucine (Glu(OME)/Leu) were prepared with the following mole ratios: 85/15; 44/56; 50/50. These polymers have been used as described above under (d) to (e) for preparing other modifications of the first internal layer for the present resorbable membrane applicable to wound-dressing.

(B) Preparation of the second layer of the artificial skin

Fourteen grams of a statistical polymer of L-leucine and γ-methyl-L-glutamate prepared as disclosed in part (A) of this Example (approximate monomer mole ratio=50/50) were dissolved in 69 g of THF, then 17 g of formamide were added. The solution was cooled to 0° C. and spread over a well degreased glass plate so as to form a viscous layer of about 0,5 mm thickness. The solvents were allowed to evaporate for about 2 min. in air, then the plate was placed in an agitated ice-cold water bath and allowed to stand therein for about 1 hr. Thus, there was formed on the plate a porous semi-permeable membrane with assymetrical structure the pores openings of which had a dimension in the region of 0,001 to 0,01μ on the side of the glass plate and which were practically undepictable on the other side even with the best magnification factor. This film which was about 45μ thick (0,045 mm) was self-pulling off the glass plate.

This film will allow a flow of 0.75 ml/min.cm² of water to pass when under about 1.5 bar of pressure. It has the following rejection coefficients, expressed as percents during an ultrafiltration experiment:

| Product | % rejection |
| --- | --- |
| Aqueous solution of NaCl (5% in $H_2O$) | 0 |
| Bovine albumine | 35 |
| Polyvinylpyrrolidone (MW ~ 360,000) | 96 |

(C) Final assembly, sterilization and storage of the artificial skin

The two layers, the preparation and the properties of which have been described above, were assembled together by glueing the second one, coarser porous side down, on the first one using a minimum of a concentrated adhesive solution of glycine-N-carboxyanhydride in ethyl acetate. After drying the composite, the existence of the adhesive was not detectable anymore. Finally, the composite was sterilized by exposing 20 min. to dry $H_2O$ vapor at 140° C.

After sterilization, the artificial skin was ready for use on wounds and could be stored for extended periods (several months) after humidification with glycerol or physiological serum and sterile packing.

EXAMPLE 2

A. Preparation of the first layer (aspartic acid-leucine type)

(a) Preparation of β-benzyl aspartate-N-carboxyanhydride

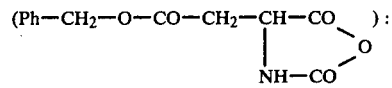

The same procedure outlined under Example 1, paragraph (A)(a) was followed which provided 20 g of the desired N-carboxyanhydride (M.p. 100° C.) from 20 g of β-benzyl aspartate.

(b) Leucine-N-carboxyanhydride: see procedure of Example 1, paragraph (A)(b).

(c) Copolymerization of a 50/50 molar mixture of the N-carboxyanhydrides of L-leucine and β-benzyl-L-aspartate: This was carried out using a solution of 26 g of the aspartate derivative and 16,3 g of the leucine compound in a mixture of 560 ml Bz and 140 ml dioxane. The method was identical to that of Example 1, paragraph (A)(c) using 100 mg of triethylamine and 1 g of NaH. After 24 hrs, the NaH was filtered off and the solution was used directly for the next step.

(d) Transesterification: 610 ml of benzene (Bz) were used to dilute and decrease the viscosity of the above solution, then at 65° C. a solution of 17,4 ml $H_2SO_4$ 98% in 430 ml methanol (MeOH) was added with stirring. After 60 hrs at reflux temperature, the mixture was concentrated under vacuum until the polymer separated by precipitation. The solid was dissolved in 100 ml THF, then the solution was filtered with diluted with 2 l. of water which caused the polymer to precipitate. The solid was collected washed with water and dried at 50° C. Then it was purified by redissolving with 100 ml DCA, precipitating with $H_2O$, washing until neutral and drying. Thus, 20 g of the copolymer poly(β-methyl-L-aspartate-leucine) with a 50/50 molar ratio, comprising a 3% residual benzyl groups (ascertained by NMR analysis) were obtained.

(e) Preparation of the pluricellular material: 3 g of the above copolymer were dissolved in a mixture of 14 g of $CHCl_3$ and 20 g of Bz. Then 18 g of NaCl finely ground in a mortar were added and mixed thoroughly. The resulting paste was spread out on a plate as in the previous example, then it was dried. Finally it was washed with running water until no salt remained and, thereafter, dried at 60° C.

(f) Saponfication and cross-linking: the plate was dipped into an absolute ethanol 1 N NaOH solution and maintained therein 24 hrs under mild agitation. The resulting spongy polymer was washed with absolute ethanol and a sample was analyzed by titration for its content in free carboxylic groups. It was found that 50% of the methyl groups has been hydrolyzed.

Thereafter, the plate was maintained 18 hrs at 70° C. in a 0,5 N solution of $H_2SO_4$ in polyoxyethylene glycol 300. After thoroughly washing with running water, the content in free —COOH groups was again measured and found to be 26%. Therefore, 24% of said —COOH groups had now been esterified by the polyoxyethylene glycol. After cross-linking and drying, the resulting foam-like material was flexible and resistant.

(B) and (C) Preparation of the second layer and assembling to the first one for making the artificial skin:

These operations were performed exactly as described in Example 1, parts (B) and (C) and gave a product with similar permeability and storage properties.

EXAMPLE 3

The various modifications of the "artificial skins" obtained according to Examples 1 and 2 have been subjected to the following use tests:

Three samples of artificial skins, respectively A, B and C were prepared as described but using, as the polymers of the first layer to be constructed with the wound, the following compositions:

A: poly(leu-Asp), (50/50); saponification level 25 mole %, i.e. half of the ester groups of the original methyl aspartate had been hydrolyzed; cross-links 0%.

B: poly(leu-Asp), (50/50); saponification 25 mole %; cross links 17,5 mole % (hence, free —COOH 17,5 mole %).

C: poly(leu-Asp), (50/50); saponficiation 40 mole %; cross-links 5 mole % (hence, free —COOH 35 mole %).

It should be mentioned that the first layer of sample A has been prepared according to the procedure of Example 2 except for the cross-linking operation which was omitted.

The samples were sterilized 2 hrs under UV after which pieces (10×5 mm and 2,5 mm thick) were cut therefrom and applied to male Wistar rats that had been incised in the shoulder region. After a period ranging from 24 hrs to 3 weeks, the animals were sacrificed and the degree of resorption of the material of the internal layer of the dressings was visually estimated and expressed as the percent of the original spongy tissue having been effectively degraded. The results are shown in the following Table.

| Sample | Resorption time | | |
|---|---|---|---|
| | 24 hrs | 10 days | 3 weeks |
| A | 28% | 70% | 100% |
| B | 1% | 10% | 20% |
| C | 35% | 100% | — |

These results clearly show that the resorption rate grows in proportion with the free —COOH content, i.e. the saponification level and that it decreases with an increasing degree of cross-linking. Each of such parameters can be adjusted according to the directions given herein and it is consequently possible to prepare a full range of artificial skins with different resorption rates which will fit individual needs.

On the other hand, when the aspartic unit in the above polymers was replaced by corresponding glutamic units, the overall resorption rate of the products was significantly augmented.

I claim:

1. Synthetic membrane or skin containing polyaminoacids usable for wound-dressings consisting of two integral layers of which at least one is resorbable by the body, the first internal layer being directly applied to the wound and the second layer constituting an external protection thereof, characterized by the fact that the second layer is formed from a porous semi-permeable membrane or film having an asymmetric structure, that is having pores of decreasing size when going from the inside layer to the outside one, which ensures the free penetration of air, water and low molecular weight substances but prevents the entrance of external pathogenic germs, and by the fact that the first layer is essentially formed of a hydrophilic, non-toxic, bio-degradable membrane or tissue consisting substantially of a pluri-cellular, spongy and fluid permeable material selected from polymers and copolymers of α-aminoacids and esters thereof.

2. The membrane of claim 1, wherein said first layer comprises a copolymer of L-leucine and L-glutamic acid partially esterified.

3. The membrane of claims 2 wherein the copolymer of said first layer is cross-linked by means of ester bridges resulting from an esterification of the —COOH functions with a diol, e.g. polyoxyethyleneglycol 300.

4. The membrane of claim 3 wherein the copolymer contains at least 10% and no more than 50 mole % of L-leucine, the rest being the said L-glutamic acid.

5. The membrane of claim 3, wherein said diol is polyoxyethyleneglycol 300.

6. The membrane of claim 1, wherein said first layer comprises a copolymer of L-leucine and L-aspartic acid partially esterified.

7. The membrane of claim 6 wherein the copolymer of said first layer is cross-linked by means of ester bridges resulting from esterification of the —COOH functions with a diol.

8. The membrane of claim 7, wherein said diol is polyoxyethyleneglycol 300.

9. The membrane of claim 7 wherein the copolymer contains at least 10% and no more than 50 mole % of L-leucine, the rest being the said aspartic acid.

10. The membrane of claim 1, wherein said first layer is 0,5–3 mm thick.

11. The membrane of claim 1, wherein the second layer comprises a material selected from film-making polymers and copolymers of α-aminoacids and alkyl esters thereof.

12. The membrane of claim 11, wherein said second layer comprises a copolymer of L-leucine and a γ-alkyl-L-glutamate.

13. The membrane of claim 12 wherein the γ-alkyl-L-glutamate is γ-methyl-L-glutamate.

14. The membrane of claim 11, wherein said second layer copolymer comprises equal mole proportions of each starting monomer.

15. The membrane of claim 11, wherein said second layer is about 30–100μ thick.

16. The use of the synthetic membrane of claim 1 as a wound-dressing that is resorbable at least in part in situ.

17. A method for manufacturing the synthetic membrane of claim 1, which comprises applying on the first layer, after said first layer has been formed, the second layer or the substance of said second layer in a manner such that the surface of the latter which has the coarser porosity will adhere to the first layer.

18. The method of claim 14, which comprises depositing on one of the surfaces of the first layer a glueing solution containing a N-carboxyanhydride of an aminoacid dissolved in an organic solvent, stacking the second layer, coarser porous side down, over the surface of the first layer coated with the adhesive with application of slight pressure and allowing the complete composite to dry until all solvent of the adhesive has evaporated.

19. The method of claim 18, wherein the aminoacid is glycine and the solvent is ethylacetate.

20. The method of claim 17, which comprises depositing on the first layer a solution of the copolymer of the second layer dissolved in a water-soluble solvent and treating the resulting composite with ice-water for a time sufficient for the solvent to fully diffuse into the water and the second layer to solidify.

* * * * *